(12) United States Patent
King et al.

(10) Patent No.: US 8,755,586 B2
(45) Date of Patent: Jun. 17, 2014

(54) IMAGE RECONSTRUCTION INCLUDING SHIFT-VARIANT BLUR COMPENSATION

(75) Inventors: Michael A. King, Northboro, MA (US);
Joyeeta Mitra Mukherjee, Worcester, MA (US); Lingxiong Shao, Saratoga, CA (US); Xiyun Song, Santa Clara, CA (US); Jiong Wang, Santa Clara, CA (US)

(73) Assignee: Koninklijke Philips N.V., Eindhoven (NL)

( * ) Notice: Subject to any disclaimer, the term of this patent is extended or adjusted under 35 U.S.C. 154(b) by 264 days.

(21) Appl. No.: 13/383,584

(22) PCT Filed: Jun. 15, 2010

(86) PCT No.: PCT/IB2010/052678
§ 371 (c)(1),
(2), (4) Date: Jan. 12, 2012

(87) PCT Pub. No.: WO2011/007270
PCT Pub. Date: Jan. 20, 2011

(65) Prior Publication Data
US 2012/0114212 A1    May 10, 2012

Related U.S. Application Data

(60) Provisional application No. 61/225,237, filed on Jul. 14, 2009.

(51) Int. Cl.
*G06K 9/00* (2006.01)

(52) U.S. Cl.
USPC .......................................... 382/131

(58) Field of Classification Search
None
See application file for complete search history.

(56) References Cited

U.S. PATENT DOCUMENTS

| | | | |
|---|---|---|---|
| 5,909,476 A * | 6/1999 | Cheng et al. | 378/4 |
| 7,583,780 B2 * | 9/2009 | Hsieh et al. | 378/4 |
| 2006/0098857 A1 * | 5/2006 | Hawman | 382/131 |
| 2006/0101106 A1 | 5/2006 | Subbarao | |
| 2008/0037846 A1 | 2/2008 | Avinash et al. | |
| 2008/0166063 A1 * | 7/2008 | Zeng | 382/260 |
| 2008/0199063 A1 * | 8/2008 | O'Halloran et al. | 382/131 |

OTHER PUBLICATIONS

Avinash, G., et al.; Characterization of point spread function in linear digital tomosynthesis: A simulation study; 2006; Medical Imaging; vol. 6142; 8 pages.

Israni, K., et al.; Point Spread Function based classification of regions for Linear Digital Tomosynthesis; 2007; Physics of Medical Imaging; vol. 6510, No. 29; 12 pages.

* cited by examiner

*Primary Examiner* — Jason M Repko
*Assistant Examiner* — Shervin Nakhjavan (57) ABSTRACT

An image reconstruction method comprises reconstructing an image using an iterative reconstruction method and computing a projection used in the reconstructing by summing ray increments between neighboring planes (P0, P1, P2, . . . ) parallel with a detector face (42) with stationary incremental blurring associated with each ray increment computed based on a distance between the neighboring parallel planes. A non-stationary blurring kernel may also be convolved at a plane closest to the detector face to generate a projection incorporating shift-variant blurring.

19 Claims, 4 Drawing Sheets

IMAGE RECONSTRUCTION INCLUDING SHIFT-VARIANT BLUR COMPENSATION

CROSS REFERENCE TO RELATED APPLICATIONS

This application claims the benefit of U.S. provisional application Ser. No. 61/225,237 filed Jul. 14, 2009, which is incorporated herein by reference.

The following relates to the imaging arts, medical imaging arts, image processing arts, medical image processing arts, and related arts.

Blur due to finite detector resolution is present in imaging modalities such as single photon emission computed tomography (SPECT) imaging, positron emission tomography (PET) imaging, transmission computed tomography (CT) imaging, and other imaging modalities. Using SPECT imaging as an illustrative example, if an ideal point radiation emission source is imaged by a gamma camera, the image is blurred due to finite collimation openings of the radiation collimator. For fan-beam or cone-beam collimators, the blurring is spatially dependent both on distance from the collimator/detector assembly and on lateral location across the face of the collimator/detector assembly. In PET, similar blurring results due to finite spatial accuracy (that is, non-zero area or volume localization) of 511 keV gamma ray detection events in the scintillator crystal. Finite spatial accuracy is also extant in CT imaging.

Blurring can be addressed on the hardware side by improved imaging system design. For example, in SPECT longer collimator openings can improve the collimation to reduce blurring, albeit at the expense of reduced count rate. In PET, Anger logic is sometimes used to enhance this spatial accuracy, but some blurring remains. In CT imaging a higher x-ray beam strength can be used, but this increases the radiation exposure of the subject. Similarly, increasing the administered dosage of radiopharmaceutical can be helpful in SPECT and PET. However, for imaging of human subjects, safety considerations and jurisdictional government regulations typically limit the allowable x-ray exposure or radiopharmaceutical dosage.

Blurring can also be mathematically compensated during the image reconstruction process. Some existing blur compensation techniques for fan-beam SPECT imaging are shift-invariant, meaning that they account for the distance dependence of the blurring but assume that the blurring is not dependent on the lateral location across the face of the collimator/detector assembly.

The following provides new and improved apparatuses and methods which overcome the above-referenced problems and others.

In accordance with one disclosed aspect, an apparatus comprises: a ray tracing module comprising a digital processor configured to perform a projection operation for a detector having shift-variant blurring by (i) computing ray increments between planes parallel with a detector face, (ii) computing stationary incremental blurring kernels corresponding to the ray increments, (iii) incrementally summing the ray increments convolved with the corresponding stationary incremental blurring kernels to generate a projection, and (iv) adjusting the projection for shift-variant blurring; and an iterative image reconstruction module comprising a digital processor configured to generate a reconstructed image from projection data using iterative reconstruction including projection operations performed by the ray tracing module.

In accordance with another disclosed aspect, an apparatus as set forth in the immediately preceding paragraph is disclosed, wherein the projection operation performed by the ray tracing module includes performing the adjusting (iv) by convolving with a nonstationary blurring kernel at a plane proximate to the detector face to generate the projection incorporating shift-variant blurring.

In accordance with another disclosed aspect, an image reconstruction method comprises: reconstructing an image using an iterative reconstruction method; and computing a projection used in the reconstructing by (i) computing ray increments between neighboring planes parallel with a detector face of a detector having shift-variant blurring, (ii) computing stationary incremental blurring kernels between neighboring planes parallel with the detector face based on a distance between the neighboring parallel planes, (iii) incrementally summing the ray increments convolved with corresponding stationary incremental blurring kernels to compute the projection, and (iv) adjusting the projection for shift-variant blurring.

In accordance with another disclosed aspect, an image reconstruction method as set forth in the immediately preceding paragraph is disclosed, wherein the adjusting (iv) comprises convolving with a non-stationary blurring kernel at a selected one of the neighboring planes.

In accordance with another disclosed aspect, an image reconstruction method comprises: reconstructing an image using an iterative reconstruction method; and computing a projection used in the reconstructing by (i) summing ray increments between neighboring planes parallel with a detector face of a detector having shift-variant blurring with stationary incremental blurring associated with each ray increment computed based on a distance between the neighboring parallel planes and (ii) incorporating shift variant blurring in at least one direction parallel with the neighboring parallel planes.

In accordance with another disclosed aspect, an image reconstruction method as set forth in the immediately preceding paragraph is disclosed, wherein the operation (ii) includes convolving with a nonstationary blurring kernel at a plane proximate to the detector face to incorporate shift variant blurring in at least one direction parallel with the neighboring parallel planes.

In accordance with another disclosed aspect, an image reconstruction processor is programmed to perform an image reconstruction method as set forth in any one of the four immediately preceding paragraphs. In accordance with another disclosed aspect, a storage medium stores instructions executable by a digital processor to perform an image reconstruction method as set forth in any one of the four immediately preceding paragraphs.

One advantage resides in providing computationally efficient shift-variant blur compensation.

Another advantage resides in providing improved image quality.

Further advantages will be apparent to those of ordinary skill in the art upon reading and understand the following detailed description.

Figure 1:
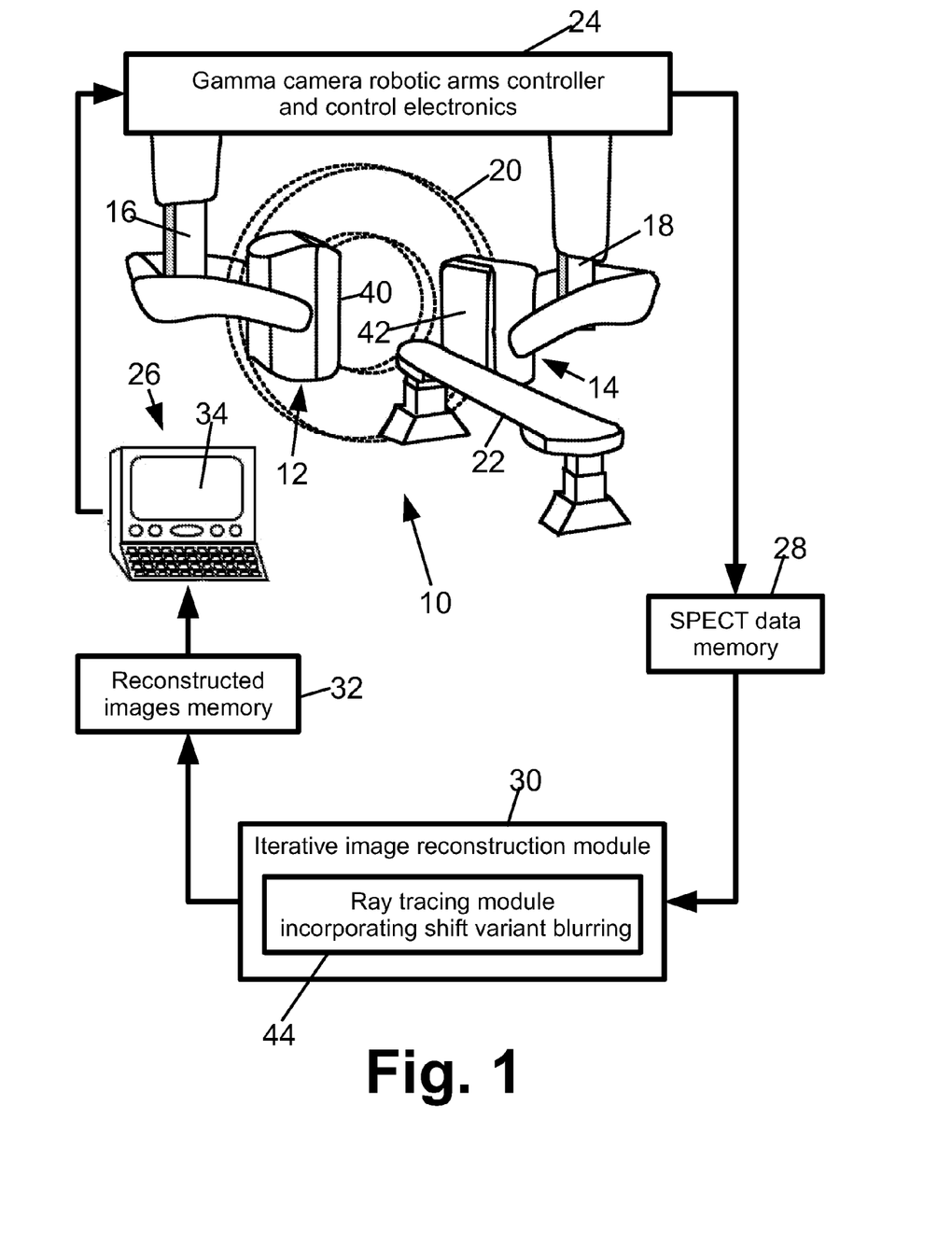
FIG. 1 diagrammatically shows an imaging system including image reconstruction incorporating shift-variant blur compensation.

With reference to FIG. 1, an imaging system includes an imaging device 10, which in the illustrated embodiment is a gamma camera configured to acquire single photon emission computed tomography (SPECT) projection data. The illustrated gamma camera 10 is substantially similar to the SKY-Light gantry-free nuclear camera available from Koninklijke Philips Electronics N.V. (Eindhoven, the Netherlands), and includes radiation detectors 12, 14 mounted on respective robotic arms 16, 18. Alternatively, a gantry-based nuclear camera can be used in which the radiation detectors 12, 14 are mounted on a gantry 20 (shown in phantom to indicate an alternative embodiment), typically along with additional manipulators to enable the radiation detectors to be rotated, tilted, or otherwise manipulated. An example of a gantry-based gamma camera is the BrightView SPECT imager also available from Koninklijke Philips Electronics N.V. (Eindhoven, the Netherlands). A subject for imaging is loaded or disposed on a subject support 22 so as to be positioned for viewing by the radiation detectors 12, 14.

The imaging device can generate projection data of another imaging modality besides SPECT, such as a positron emisson tomography (PET) scanner generating PET projection data, or a transmission computed tomography (CT) scanner generating CT projection data, or so forth. In the case of SPECT and CT, collimators are employed to spatially define the projections, whereas PET projections are defined by the simultaneous detection (or substantially simultaneous detection, in the case of time-of-flight PET) of two oppositely directed 511 keV gamma particles emitted by an electron-positron annihilation event.

In the case of SPECT and PET, a radiopharmaceutical containing a radioisotope is administered to the subject, the radiopharmaceutical preferentially collects in an organ or tissue of interest, and radiation detectors 12, 14 detect radioemissions from the radioisotope. Hence, in SPECT and PET the projection data are representative of the distribution of radiopharmaceutical in the subject. In the case of CT, an x-ray tube generates an x-ray beam that is transmitted through the subject and received by a radiation detector array after transmission through the subject. Hence, in CT the projection data are representative of x-ray absorption by the subject.

The imaging device 10 operates under the control of a controller 24, which for the illustrated robotic gamma camera 10 embodies a robotic arms controller and other control electronics. The controller 24 controls the gamma camera 10 to acquire SPECT projection data with the radiation detectors 12, 14 positioned at various points around the subject in order to acquire 180°, 360°, or another desired angular span of projection data. The projection data acquisition is typically controlled by a radiologist or other human user through the intermediary of a suitable user interface such as an illustrated computer 26. The acquired SPECT projection data are stored in a SPECT data memory 28. In the case of a PET scanner, a stationary ring of radiation detectors is typically employed. In the case of CT, a ring of detectors can be used in conjunction with an x-ray tube that revolves around the subject, or an assembly of an x-ray tube and opposingly positioned radiation detector array can be rotated such that the x-ray tube and radiation detector array rotate in concert around the subject. Other configurations of stationary or movable radiation detectors and radiation sources internal or external of the subject are also contemplated. The acquired projection data are reconstructed by an iterative image reconstruction module 30 to generate a reconstructed image that is stored in a reconstructed images memory 32, displayed on a display 34 of the illustrated computer 26 or on another display device, printed using a marking engine, transmitted via the Internet or a hospital data network, stored in a picture archiving and communication system (PACS), or otherwise utilized.

With continuing reference to FIG. 1, the illustrated gamma camera 10 employs two radiation detectors 12, 14 defining respective detector faces 40, 42. More generally, the imaging device employs one or more radiation detectors each defining one or more detector faces. In PET, for example, an annular ring of detectors is employed, whose detector faces form a piecewise approximation of a ring or cylinder around the subject. In general, a projection detected by the radiation detector 12, 14 is blurred by an amount that varies with distance away from the detector face 40, 42. For example, a physical linear collimator cannot collimate to a perfect line, but rather collimates to a narrow-angle cone, whose area expands with increasing distance from the detector face 40, 42. The detectors 12, 14 also have shift-variant blurring. In shift-variant blurring, the amount of blurring also varies with the lateral position across the detector face 40, 42 where the projection was detected. Sources of shift variance in the blurring can result from the use of fan-beam or cone-beam collimators, a fan-beam or cone-beam x-ray source in the case of transmission CT, variance in the spatial localization precision of PET detectors across the detector face, and so forth.

The iterative image reconstruction module 30 employs an iterative reconstruction algorithm. In iterative reconstruction, an initial image is adjusted in iterative fashion until it substantially comports with the acquired projection data. In some such algorithms, the initial image may be simply a uniform distribution in the image space. To improve convergence, a priori knowledge may optionally be used to provide an initial image that is closer to the expected final image. For example, a known contour of the subject or of a portion thereof expected to be represented by the reconstructed image may be used as the initial image. In order to compare the initial image with the acquired projection data, the iterative image reconstruction module employs a ray tracing module 44 that projects the image so as to generate projection data that may be directly compared with the acquired projection data. Through the process of backprojection the initial image is adjusted based on the comparison of the projected initial image and acquired projection data to generate an improved image. The improved image is again projected by the ray tracing module 44 and compared with the acquired projection data, further image adjustment is made, and so forth in iterative fashion until the iteratively improved image when projected by the ray tracing module 44 is sufficiently close to the acquired projection data, as measured by a suitable stopping criterion.

To provide a more accurate reconstruction, the ray tracing module 44 of FIG. 1 incorporates blurring. In other words, in computing projections of the image the ray tracing module 44 introduces blurring into the projection so as to mimic the blurring expected to have been incorporated into the acquired projection data due to physical limitations in the collimation or other sources of blurring.

Figure 2:
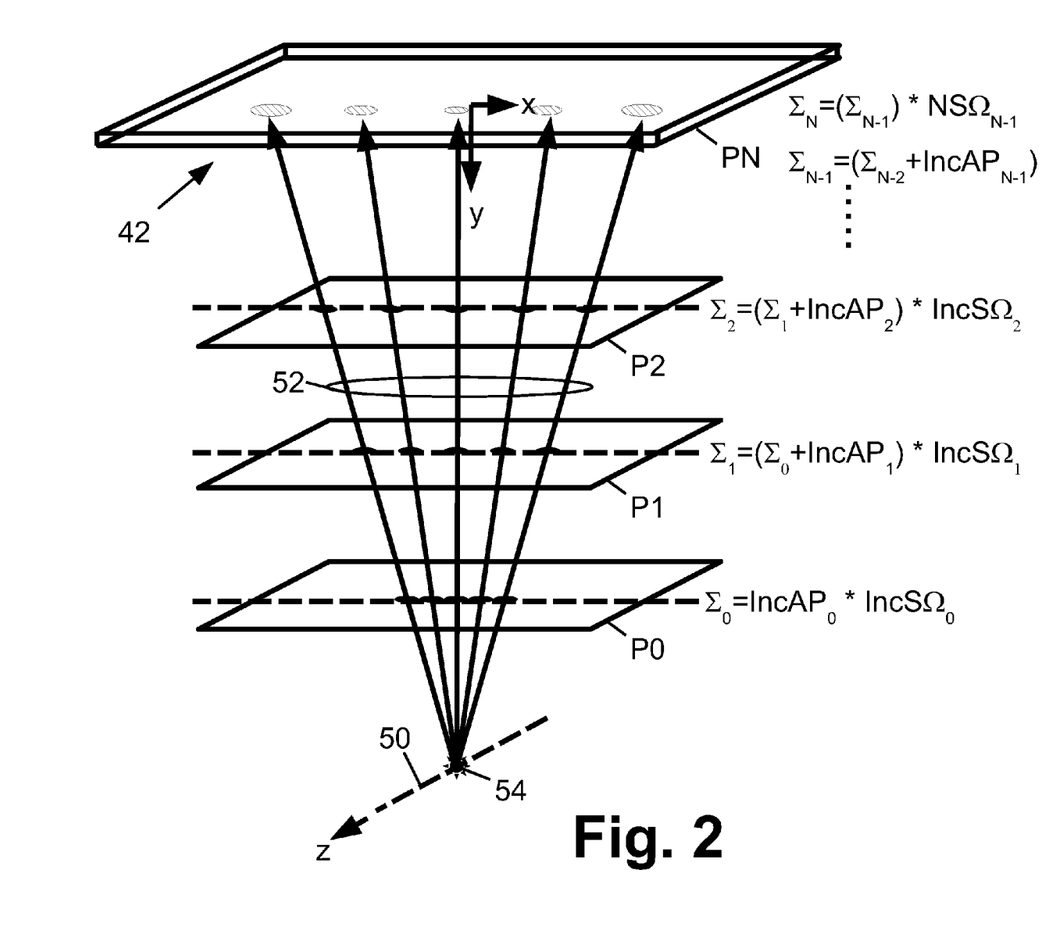
FIG. 2 diagrammatically shows a projection operation computed by iterative ray-tracing and including shift-variant blurring.

With continuing reference to FIG. 1 and with further reference to FIG. 2, operation of the ray tracing module 44 is further described. In the following, operation of the ray tracing module 44 as a projector is described, but operation as a backprojector is analogous. FIG. 2 diagrammatically depicts the detector face 42 of the radiation detector 14 of FIG. 1, which in the illustrative example shown in FIG. 2 is assumed to provide fan beam collimation. A coordinate system is selected in which distance away from the detector face 42 is measured along a coordinate y oriented transverse to the detector face 42. The fan beam collimation is along a coordinate x oriented parallel with the detector face 42. The fan beam collimation has a focal line 50 lying transverse to both the x and y coordinates. For illustrative purposes a set of projections 52 are shown emanating from a point 54 lying on the focal line 50. A projection is computed by dividing the space between the source 54 and the detector face 42 that contains a subject into a plurality of parallel planes each of which is parallel with the detector face 42. For illustrative purposes, FIG. 2 illustrates three such planes denoted P0, P1, P2. Without loss of generality it is assumed that there are N such planes numbers 0, . . . , N−1 through the imaging subject (or other element in the field of view that contributes to the projection). The detector face 42 is coincident with an $N^{th}$ plane which is denoted in FIG. 2 as PN. The planes P0, P1, P2, . . . , PN are parallel to each other and to the detector face 42 and a ray-tracing projection technique is used to compute the projection. The y direction is transverse to the planes P0, P1, P2, . . . , PN and the x direction is parallel with the planes P0, P1, P2, . . . , PN.

Figure 3:
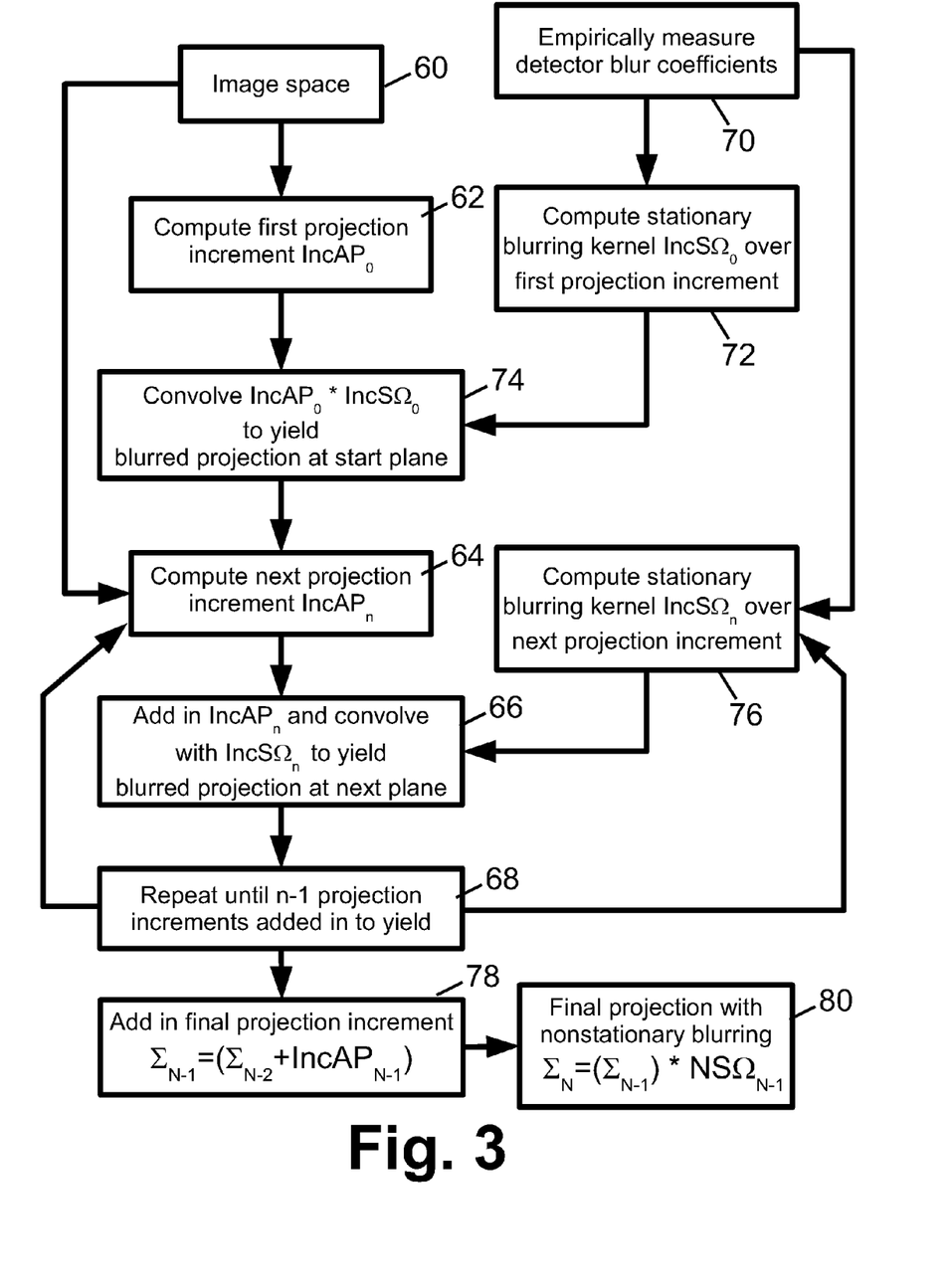
FIG. 3 diagrammatically shows operation of the ray tracing module to perform a projection operation incorporating shift-variant blurring of FIG. 1.

With continuing reference to FIGS. 1 and 2 and with further reference to FIG. 3, the ray tracing module 44 performs a projection operation to compute one of the projections 52. As an initial point of consideration, the projection is computed for a specified geometry (specified by a direction, length, and termination point on the detector face 42) in an image space 60. The image space 60 may, for example, be the initial image used to start the iterative image reconstruction, or may be one of the iteratively improved images generated during the course of the iterative reconstruction. The density in the image space 60 represents what was measured by the acquired projection data. For SPECT or PET data, the density of the image space 60 represents density of the radiopharmaceutical. For CT data, the density of the image space 60 represents x-ray absorption (or an equivalent quantity, such as an inverse of the x-ray absorption).

With continuing particular reference on FIG. 3, the projection is computed by ray tracing in iterative fashion by computing ray increments (that is, projection increments in the case of a projection operation) between successive neighboring planes P0, P1, P2, . . . parallel with the detector face 42. In FIG. 3, the projection increment from the source 54 to the first parallel plane P0 (in the image space 60) is computed in an operation 62. This first projection increment is denoted herein as IncAP$_0$. The projection increment from plane P0 to plane P1 (again, in the image space 60) is computed in an operation 64 and is denoted IncAP$_1$, and this projection increment IncAP$_1$ is added to the projection increment IncAP$_0$ from source 54 to the first parallel plane P0 in a summing operation 66. A looping operation 68 repeats the operations 64, 66 for the increments from plane P1 to plane P2 and so forth so as to add up the projection increments IncAP$_0$, IncAP$_1$, IncAP$_2$, . . . , until the increment IncAP$_{N-1}$ from plane (N−2) to the plane (N−1) is added in.

With continuing reference to FIGS. 2 and 3, incorporation of blurring is now discussed. The symbol $\sigma_x(x, y)$ is used to denote blurring along the x direction at a spatial coordinate (x, y). A non-incremental scheme for incorporating blurring is first briefly described. This non-incremental scheme is not shown in FIG. 1 or otherwise illustrated, and is described only for comparative purposes. In the non-incremental scheme, $\sigma_x(x, y)$ is computed for every parallel plane P0, P1, P2, . . . and for every intersection point of a projection with the detector face 42. As the blurring $\sigma_x(x, y)$ is in general shift-variant, the blurring in a given plane is represented by NSΩ which denotes a non-stationary blurring kernel. In this non-incremental scheme, the incremental projection IncAP for each plane is convolved with the non-stationary blurring kernel NSΩ for that plane, and this is accumulated for all planes giving the final forward projection.

The non-incremental scheme for incorporating blurring has substantial disadvantages in terms of memory utilization (since the non-stationary blurring $\sigma_x(x, y)$ must be computed and stored for every parallel plane P0, P1, P2, . . . and for every intersection point of a projection with the detector face 42). Accordingly, an incremental scheme for computing projections in context of a spatially varying detector (for example, a fan-beam detector, a cone-beam detector, or other spatially diverging detector) incorporating shift-invariant blurring is disclosed herein and is illustrated in FIGS. 2 and 3. The incremental scheme optionally further incorporates shift-variant blurring in a convolution operation with a nonstationary kernel that is performed at the plane N−1 closest to the detector face 42.

In the incremental scheme, the blurring $\sigma_x(x, y)$ is assumed to be represented by a shift-variant blur model of the detector face 42 having the form (for the illustrative case of a one-dimensional fan-beam collimation along the x direction as illustrated in FIG. 2) as follows:

$$\sigma_x(x, y) = b_{x0} + b_{xy}y + b_{xx}x \quad (1),$$

where x denotes the direction of shift variance parallel with the detector face 42, y denotes the direction normal to the detector face 42 and normal to the planes P0, P1, P2, . . . , PN parallel with the detector face 42, $b_{xy}$, $b_{x0}$, and $b_{xx}$ denote scalar blur coefficients, and $\sigma_x(x, y)$ is indicative of blurring along the x direction at a spatial coordinate (x, y). The scalar blur coefficients can be determined empirically by the controller 24 causing the imaging device 10 to acquire calibration projection data using the radiation detector 14 defining the detector face 42. The controller 24 then generates the shift-variant blur model of the detector face 42 based on the acquired calibration projection data.

In a suitable approach, the detector response function (that is, the shift-variant blur model) of a fan-beam collimator is suitably measured using a plurality (e.g., 8) of linear radiation sources (such as $^{99m}$Tc filled line-sources) positioned in front of the detector face 42 in two orientations: parallel to the camera rotation axis for measurement of blur in the fan or x direction, and parallel to the fan or x direction for measurement of blur in the direction transverse to both the x direction and the y direction (denoted herein as the z direction). In an illustrative example that was actually performed, to provide data for modeling distance-dependent resolution, the line-sources were 1.14 mm in inner diameter and were imaged at multiple distances from the collimator, ranging from 3 to 28 cm at 5 cm intervals. Each line source was fitted with a series of Gaussian functions perpendicular to the line, and the average CS of all Gaussians fitted to each line source was obtained. The number of lines in the field of view (FOV) in the fan-direction reduced with the distance from the detector face 42 such that only 3 lines were visible at the maximum y-distance. Thus, only 39 data points were used for estimating the blurring $\sigma_x$ along the x-direction. This process was repeated for the horizontally-oriented line sources to estimate $\sigma_z$. The measured blurring were compared to those derived analytically including the effect of hole-elongation. Note that the measured detector response function includes the intrinsic resolution of the detector. A regression model for $\sigma_x$ was determined as a function of lateral distance along the x-direction from the center of the detector face 42, and as a function of the distance away from the detector face 42 along the y-direction, to obtain fitted values for the scalar blur coefficients $b_{xy}$, $b_{x0}$, and $b_{xx}$ of Equation (1).

Figure 4:
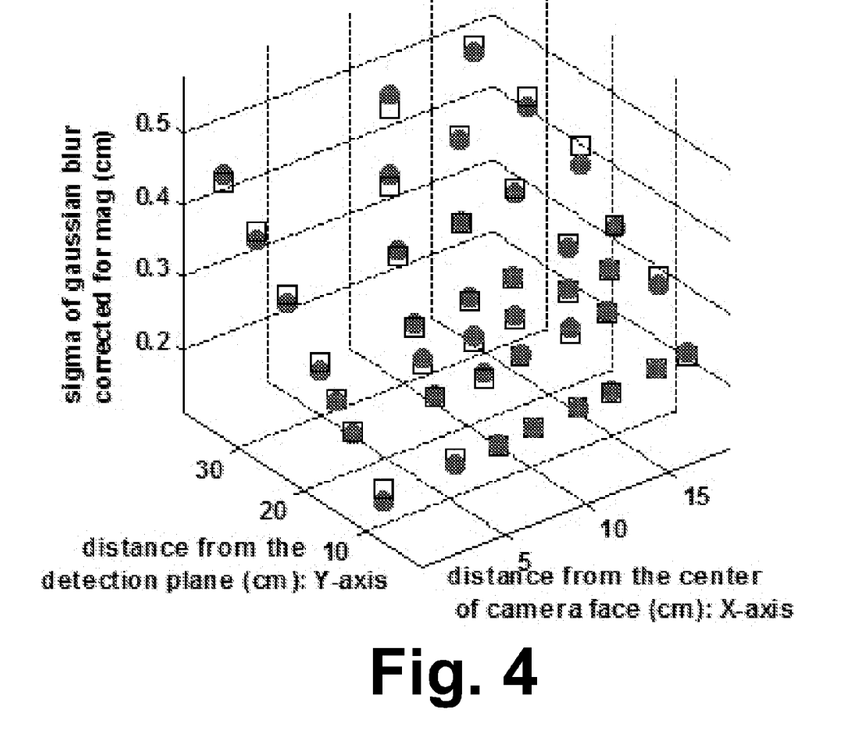
FIG. 4 diagrammatically shows a linear regression fit of the sigma of Gaussian blur corrected for magnification.

With brief reference to FIG. 4, the variation is shown of the blur standard deviation $\sigma_x$ (not including magnification) for a fan-beam collimator with the distance along the y direction from the collimator backplane and the distance from the center of the detector face along the x direction. The points obtained from the regression fit are shown as filled circles, while the measured data points are shown by squares. The sensitivity of the collimator was found to vary only slightly across the face (<1%).

With continuing reference to FIG. 2, in the incremental scheme, the incremental blur between consecutive (that is, neighboring) parallel planes is the same for all projection increments going between the parallel planes. This may be observed from the blur model in Equation (1) where for any single projection the $b_{xx}x$ term is constant from one parallel plane to the next neighboring parallel plane. Based on this observation, the shift-variant blur component is processed separately from the shift-invariant blur component. In this approach, the incremental blur between neighboring parallel planes for each projection increment is considered to be the shift-invariant (and therefore stationary) blur component which only varies with the vertical distance (that is, the distance along the y direction) between the planes. This distance is denoted herein as $\Delta y$. The stationary incremental blurring kernel between a plane indexed n and the next neighboring plane indexed n+1 is denoted by $IncS\Omega_n$ and is given by:

$$IncS\Omega_n = \sigma_{inc}^{n \to (n+1)} = \sqrt{b_{xy}^2(\Delta y)^2 + 2b_{xy}\sigma_x^{n+1}(\Delta y)} \quad (2).$$

Said another way, $IncS\Omega_n$ denotes the incremental blurring kernel applied to the projection increment $IncAP_n$ between planes n−1 and n.

With continuing reference to FIGS. 2 and 3, shift-invariant blurring can be incorporated into the projection of a detector having shift-variant blurring based on this incremental blurring concept as shown in FIG. 3. The detector blur coefficients $b_{xy}$, $b_{x0}$, and $b_{xx}$ of Equation (1) are determined empirically in an operation 70. The stationary blurring kernel $IncS\Omega_0$ corresponding to the first projection increment $IncAP_0$ is computed in an operation 72. The first projection increment $IncAP_0$ is convolved with the corresponding stationary blurring kernel $IncS\Omega_o$ in an operation 74. This is suitably represented mathematically as:

$$\Sigma_0 = IncAP_0 * IncS\Omega_0 \quad (3),$$

where the symbol "*" is used herein to denote the convolution operation. In other words, $\Sigma_0$ represents the blurred version of the first projection increment $IncAP_0$. More generally, in an operation 76 the stationary blurring kernel $IncS\Omega_n$ corresponding to the projection increment $IncAP_n$ is computed based on the shift-variant blur model of the detector face 42 (for example, as given in Equation (1) for the illustrative fan beam collimator), and the summation operation 66 is modified to incrementally sum the projection increments $IncAP_n$ convolved with the corresponding incremental blurring kernels $IncS\Omega_n$ up until the the projection increment from plane (N−3) to plane (N−2). In more mathematical terms, the incremental blurring scheme implemented as illustrated in FIG. 3 can be stated as follows. The incremental summing 66 performed by the ray tracing module 44 computes projection values quantitatively equivalent to $\Sigma_n = (\Sigma_{n-1} + IncAP_n) * IncS\Omega_n$ for n=0, ..., N−2 where n indexes the planes P0, P1, P2, ... parallel with the detector face 42, $IncAP_n$ denotes the projection increment between the planes indexed n and n−1, and $incS\Omega_n$ denotes the corresponding incremental blurring kernel (computed in Equation (2) in the illustrative fan-beam collimator example).

The last projection increment from plane (N−2) to plane (N−1) is handled slightly differently. Because the subject (or other element contributing to the projection) ends at plane N−1, there is no stationary incremental blurring component $IncS\Omega_{N-1}$. Accordingly, in an operation 78 the last projection increment (reaching the detector) is added in as $\Sigma_{N-1} = (\Sigma_{N-2} + IncAP_{N-1})$.

The projection at the detector element including shift-invariant blurring is the output of operation 80 but with a stationary blurring kernel corresponding to plane N−1 $\Sigma_N = (E_{N-1}) * S\Omega_{N-1}$. In some embodiments, this is deemed sufficiently accurate and is taken as the final projection. In other words, in these embodiments the shift-variant blurring component of the detectors 12, 14 having shift-variant blurring is neglected, and the computed projection compensated for shift-invariant blurring is deemed to have acceptable accuracy.

Alternatively, the nonstationary blurring component of Equation (1) can also be taken into account in order to compensate for blurring including both the shift-invariant and the shift-variant blurring components. This is done taking into account the observation that for any single projection the $b_{xx}x$ term is constant from one parallel plane to the next neighboring parallel plane. As a result, the shift-variant component of the blurring can be accounted for by computing it for the last plane of the subject, that is, for the plane N−1. This is done in FIG. 3 in operation 80 which applies the nonstationary blurring $NS\Omega_{N-1}$ at plane N−1 to the final projection according to the expression $\Sigma_N = (\Sigma_{N-1}) * NS\Omega_{N-1}$, where the nonstationary blurring $NS\Omega_{N-1}$ at plane N−1 is given by evaluating Equation (1) at the plane N−1, in order to yield the final projection including shift-variant blurring.

Operation of the ray tracing module 44 to perform a backprojection operation operates in the inverse way. In the case of backprojection, the final projection (without blurring) is the starting point, and the ray tracing starts at the plane N−1 closest to the detector and works backward to the initial plane 0. The incremental blurring kernel is used to incrementally add in stationary blurring for each ray increment (that is, backprojection increment in the backprojection case). The final backprojection is the image content with shift invariant blurring. If it is desired to incorporate shift variant blurring, then the nonstationary kernel is first introduced by convolution at the plane N−1 closest to the detector, so that the final backprojection is the image content with shift variant blurring.

The illustrative example is readily modified to incorporate other blur models that model other types of detector faces. For example, the shift-variant blur model of the detector face may include shift variance in two nonparallel directions both parallel with the detector face. This is appropriate, for example, to model a detector face having cone-beam collimation. In this case, the shift variant blur model includes a term $\sigma_\alpha(\alpha, \beta, y)$ indicative of blurring along the $\alpha$ direction at a spatial coordinate $(\alpha, \beta, y)$ of the form $b_{\alpha 0} + b_{\alpha y} + b_{\alpha\alpha}\alpha$ where $\alpha$ denotes one of the two directions of shift variance parallel with the detector face, y denotes a direction normal to the detector face and normal to the planes parallel with the detector face, and $b_{\alpha y}$, $b_{\alpha 0}$, and $b_{\alpha\alpha}$ denote scalar blur coefficients. The shift variant blur model further includes a term $\sigma_\beta(\alpha, \beta, y)$ indicative of blurring along the $\beta$ direction at a spatial coordinate $(\alpha, \beta, y)$ of the form $b_{\beta 0} + b_{\beta y}y + b_{\beta\beta}\beta$ where $\beta$ denotes the other of the two directions of shift variance parallel with the detector face and $b_{\beta y}$, $b_{\beta 0}$, and $b_{\beta\beta}$ denote scalar blur coefficients. Again, the incremental blur between consecutive (that is, neighboring) parallel planes is the same for all ray increments going between the parallel planes for a given projection, as observed from the blur model where for any single ray increment the $b_{\alpha\alpha}\alpha$ and $b_{\beta\beta}\beta$ terms are each constant from one parallel plane to the next neighboring parallel plane. The stationary incremental blurring can then be written analogously to that shown in Equation (2), and the incremental summing $\Sigma_n=(\Sigma_{n-1}+\mathrm{IncAP}_n)*\mathrm{IncS}\Omega_n$ applied as in the illustrated embodiment, optionally followed by a final incorporation of the nonstationary blurring component through the convolution operation $\Sigma_N=(\Sigma_{N-1})*\mathrm{NS}\Omega_{N-1}$ of the operation 80 of FIG. 3.

Figure 5:
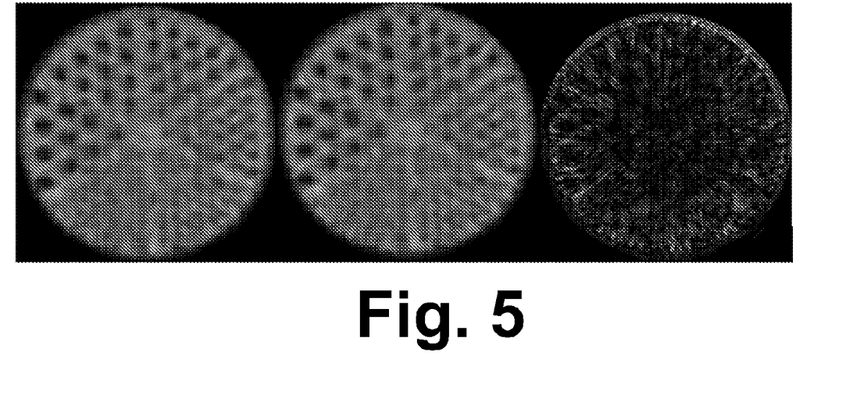
FIG. 5 shows imaging results acquired for a phantom.

With reference to FIG. 5, a comparison is shown of an image reconstruction of projection data acquired of a phantom reconstructed using shift variant versus shift invariant blur compensation. A Data Spectrum QC phantom was used. FIG. 5 shows the same image slices taken from the reconstructed images of the QC phantom, with and without shift-variant blur compensation. The left-most image was reconstructed with shift-invariant blur compensation. The middle image was reconstructed with shift-variant blur compensation. The right-most image is the difference image. The images were reconstructed with a smaller pixel size (~60%) than acquired, thus the difference image shows no significant change in the reconstructed image. However, note the clearer definition of the holes near the outside of the phantom and in the 5th smallest rod size with use of shift variant modeling across the face in reconstruction.

The incremental blur scheme is more efficient in terms of computational speed and memory usage for implementation of shift-variant blur compensation. The computational speed is 1.5 times that of the non-incremental. The memory usage is only about 1% of that in non-incremental scheme.

With returning reference to FIG. 1, the iterative image reconstruction module 30 including the ray tracing module 44 incorporating shift variant blurring using the incremental blurring approach disclosed herein is suitably embodied by a digital processor programmed to perform the iterative image reconstructioin including the projection operation including blurring as described with reference to FIGS. 2 and 3. The digital processor may, for example, be embodied by a central processing unit (which may be a multi-core processing unit) of the computer 26, or by graphical processing unit (GPU), microprocessor, microcontroller, or so forth, or by various combinations thereof. The components 30, 44 may be embodied by a single processor or by separate processors. Moreover, the disclosed techniques may be embodied as a storage medium storing instructions executable by a digital processor to perform an image reconstruction method including blur compensation as set forth herein. The storage medium may, for example, include one or more of the following: a hard disk drive or other magnetic storage medium; an optical disk or other optical storage medium; a random access memory (RAM), read-only memory (ROM), flash memory, or other electronic storage medium; or so forth.

This application has described one or more preferred embodiments. Modifications and alterations may occur to others upon reading and understanding the preceding detailed description. It is intended that the application be construed as including all such modifications and alterations insofar as they come within the scope of the appended claims or the equivalents thereof.

Having thus described the preferred embodiments, the invention is now claimed to be:

1. An apparatus comprising:
    a ray tracing module comprising a digital processor configured to perform a projection operation for a detector having shift-variant blurring by (i) computing ray increments between planes parallel with a detector face of the detector, (ii) computing stationary incremental blurring kernels corresponding to the ray increments, (iii) incrementally summing the ray increments convolved with the corresponding stationary incremental blurring kernels to generate a projection, and (iv) adjusting the projection for shift-variant blurring by convolving with a nonstationary blurring kernel at a plane proximate to the detector face to generate the projection incorporating shift-variant blurring; and
    an iterative image reconstruction module comprising a digital processor configured to generate a reconstructed image from projection data using iterative reconstruction including projection operations performed by the ray tracing module.

2. The apparatus as set forth in claim 1, wherein the nonstationary blurring kernel includes shift variance in one direction parallel with the detector face.

3. The apparatus as set forth in claim 2, wherein the nonstationary blurring kernel models a fan-beam collimator.

4. The apparatus as set forth in claim 1, wherein nonstationary blurring kernel includes shift variance in two nonparallel directions both parallel with the detector face.

5. The apparatus as set forth in claim 4, wherein the shift-variant blur model of the detector face models a cone-beam collimator.

6. The apparatus as set forth in claim 1, further comprising:
    an imaging device including a radiation detector defining the detector face; and
    a controller comprising control electronics configured to cause the imaging device to acquire projection data and to cause the iterative image reconstruction module to generate a reconstructed image from the acquired projection data.

7. The apparatus as set forth in claim 6, wherein the controller is further configured to cause the imaging device to acquire calibration projection data using the radiation detector defining the detector face and wherein the controller is further configured to generate the blurring kernels based on the acquired calibration projection data.

8. The apparatus as set forth in claim 6, wherein the imaging device comprises one of (i) a gamma camera configured to perform single photon emission computed tomography (SPECT) imaging, (ii) a positron emission tomography (PET) scanner, and (iii) a transmission computed tomography (CT) scanner.

9. The apparatus as set forth in claim 1, wherein the operation of computing stationary incremental blurring kernels corresponding to the ray increments is spatially dependent only on a coordinate y along a direction normal to the detector face and normal to the planes parallel with the detector face.

10. The apparatus as set forth in claim 1, wherein for a ray increment between neighboring planes parallel with the detector face, the corresponding stationary incremental blurring kernel is spatially dependent only on a distance $\Delta y$ between the neighboring planes.

11. An image reconstruction method comprising:
    reconstructing an image using an iterative reconstruction method; and
    computing a projection used in the reconstructing by (i) computing ray increments between neighboring planes parallel with a detector face of a detector having shift-variant blurring, (ii) computing stationary incremental blurring kernels between neighboring planes parallel with the detector face based on a distance between the neighboring parallel planes, (iii) incrementally summing the ray increments convolved with corresponding stationary incremental blurring kernels to compute the projection, and (iv) adjusting the projection for shift-variant blurring.

12. The image reconstruction method as set forth in claim 11, wherein the computing a projection used in the reconstruction comprises:
(i) computing ray increments $IncAP_n$ between neighboring planes parallel with the detector face;
(ii) computing incremental blurring kernels $IncS\Omega_n$ between neighboring planes parallel with the detector face based on the distance between the neighboring parallel planes; and
(iii) incrementally summing the ray increments convolved with corresponding incremental blurring kernels.

13. The image reconstruction method as set forth in claim 11, wherein the adjusting (iv) comprises:
convolving with a non-stationary blurring kernel at a selected one of the neighboring planes.

14. The image reconstruction method as set forth in claim 11, wherein the reconstructing and computing are performed by a digital processor.

15. An image reconstruction method comprising:
reconstructing an image using an iterative reconstruction method; and
computing a projection used in the reconstructing by (i) summing ray increments between neighboring planes parallel with a detector face of a detector having shift-variant blurring with stationary incremental blurring associated with each ray increment computed based on a distance between the neighboring parallel planes and (ii) incorporating shift variant blurring in at least one direction parallel with the neighboring parallel planes.

16. The image reconstruction method as set forth in claim 15, wherein the stationary incremental blurring associated with each ray increment is independent of position of the ray increment in any direction parallel with the parallel planes.

17. The image reconstruction method as set forth in claim 15, wherein the operation (ii) comprises:
convolving with a nonstationary blurring kernel at a plane proximate to the detector face to incorporate shift variant blurring in at least one direction parallel with the neighboring parallel planes.

18. An image reconstruction processor programmed to perform an image reconstruction method comprising:
reconstructing an image using an iterative reconstruction method; and
computing a projection used in the reconstructing by (i) summing ray increments between neighboring planes parallel with a detector face of a detector having shift-variant blurring with stationary incremental blurring associated with each ray increment computed based on a distance between the neighboring parallel planes and (ii) incorporating shift variant blurring in at least one direction parallel with the neighboring parallel planes.

19. A non-transitory storage medium storing instructions executable by a digital processor to perform an image reconstruction method comprising:
reconstructing an image using an iterative reconstruction method; and
computing a projection used in the reconstructing by (i) computing ray increments between neighboring planes parallel with a detector face of a detector having shift-variant blurring, (ii) computing stationary incremental blurring kernels between neighboring planes parallel with the detector face based on a distance between the neighboring parallel planes, (iii) incrementally summing the ray increments convolved with corresponding stationary incremental blurring kernels to compute the projection, and (iv) adjusting the projection for shift-variant blurring.

* * * * *